United States Patent
Tweden et al.

(10) Patent No.: US 6,258,122 B1
(45) Date of Patent: Jul. 10, 2001

(54) BIORESORBABLE ANNULOPLASTY PROSTHESIS

(75) Inventors: Katherine S. Tweden, Mahtomedi; Peggy T. Malikowski, Shoreview, both of MN (US)

(73) Assignee: St. Jude Medical, Inc., St. Paul, MN (US)

(*) Notice: Subject to any disclaimer, the term of this patent is extended or adjusted under 35 U.S.C. 154(b) by 752 days.

(21) Appl. No.: 08/794,398

(22) Filed: Feb. 5, 1997

Related U.S. Application Data

(63) Continuation of application No. 08/551,352, filed on Nov. 1, 1995, now abandoned.

(51) Int. Cl.⁷ ........................................ A61F 2/24
(52) U.S. Cl. ........................................... 623/2.36
(58) Field of Search ..................... 623/1, 2, 900, 623/2.36

(56) References Cited

U.S. PATENT DOCUMENTS

| | | |
|---|---|---|
| 3,620,218 | 11/1971 | Schmitt et al. . |
| 3,714,671 * | 2/1973 | Edwards et al. ............. 623/900 |
| 4,042,979 * | 8/1977 | Angeli ........................ 623/2 |
| 4,055,861 * | 11/1977 | Carpentier et al. ............ 623/2 |
| 4,290,151 | 9/1981 | Massana . |
| 4,343,048 * | 8/1982 | Ross et al. .................. 623/900 |
| 4,602,911 | 7/1986 | Ahmadi et al. . |
| 4,753,652 | 6/1988 | Langer et al. . |
| 4,917,698 | 4/1990 | Carpentier et al. . |
| 5,061,277 | 10/1991 | Carpentier et al. . |
| 5,085,629 | 2/1992 | Goldberg et al. . |
| 5,201,880 * | 4/1993 | Wright et al. ................ 623/2 |
| 5,258,021 * | 11/1993 | Duran ........................ 623/2 |
| 5,306,286 | 4/1994 | Stack et al. . |
| 5,326,371 * | 7/1994 | Love et al. .................. 623/900 |
| 5,376,112 | 12/1994 | Duran . |
| 5,412,068 | 5/1995 | Tang et al. . |
| 5,464,450 * | 11/1995 | Buscemi et al. .............. 623/1 |
| 5,489,297 * | 2/1996 | Duran ........................ 623/2 |
| 5,584,879 * | 12/1996 | Reimold et al. .............. 623/2 |

FOREIGN PATENT DOCUMENTS

| | | |
|---|---|---|
| 0 338 994 A1 | 10/1989 | (EP) . |
| 0 594 148 A1 | 4/1994 | (EP) . |
| WO 95/03757 | 2/1995 | (WO) . |

OTHER PUBLICATIONS

Beck et al., "Structure and Function of Laminin: Anatomy of a Multidomain Glycoprotein", The FASEB Journal, vol. 4, pp. 149–160 (Feb. 1990).

Carpentier et al., "Reconstructive Surgery of Mitral Valve Incompetence", J. Thorac. Cardiovac. Surg., vol. 79, pp. 338–348 (1980).

Duran et al., "Clinical and Hemodynamic Performance of a Totally Flexible Prosthetic Ring for Atrioventricular Valve Reconstructive", The Annals of Thoracic Surgery, vol. 22, No. 5, pp. 458–463 (Nov. 1976).

Gorton et al., "Mitral Valve Repair Using a Flexible and Adjustable Annuloplasty Ring", Ann. Thorac. Surg., vol. 55, pp. 860–863 (1993).

Graf et al., "Identification of an Amino Acid Sequence in Laminin Mediating Cell Attachment, Chemotaxis, and Receptor", Cell, vol. 48, pp. 989–996 (1987).

(List continued on next page.)

Primary Examiner—Bruce Snow
(74) Attorney, Agent, or Firm—Hallie A. Finucane, Esq.; Peter S. Dardi; Westman, Champlin & Kelly

(57) ABSTRACT

This invention relates to heart valve annuloplasty prostheses that are fashioned of bioresorbable materials. The prostheses are eventually resorbed by the patient, during which time regenerated tissue replaces the prosthesis. This leaves the patient with a biological and functional annular structure, resulting in improved heart valve function.

2 Claims, 2 Drawing Sheets

OTHER PUBLICATIONS

Hiratzka et al., "In Vivo Comparison of Replamineform, Silastic, and Bioelectric Polyurethane Arterial Grafts", Arch. Surg., vol. 114, pp. 698–702 (Jun. 1979).

Hubbell et al., "Endothelial Cell–Selective Materials for Tissue Engineering in the Vascular Graft via a New Receptor", Dept. of Chem. Engineering, U of Texas, Austin, TX, Bio/Technology, 9:586–572 (1991).

Hubbell et al., "Tissue Engineering: the Groundwork for Development Biological Substitutes for Damaged Tissue is Being Prepared by a New, Rapidly Evolving Interdisciplinary Field that Draws on the Expertise of Chemical Engineers", C&EN, pp. 42–54 (Mar. 13, 1995).

Humphries et al., "Identification of an Alternatively Spliced Site in Human Plasma Fibronectin That Mediates Cell Type–Specific Adhesion", J. Cell Biol., vol. 103 (No. 6, Pt. 2), pp. 2637–2647 (1986).

Richard O. Hynes, "Integrins: Versatility, Modulation, and Signaling in Cell Adhesion", Cell. vol. 69, pp. 11–25 (Apr. 3, 1992).

Jamshidi et al., "Resorbable Structured Porous Materials in the Healing Process of Hard Tissue Defects", Trans. Am. Soc. Artif. Intern. Organs, vol. 34, No. 3, pp. 755–760 (1988).

Loike et al., "CD11c/CD18 on Neutrophils Recognizes a Domain at the N Terminus of the A$\alpha$ Chain of Fibrinogen" Proc. Natl. Acad. Sci., vol. 88, pp. 1044–1048 (Feb. 1991).

Murray et al., "Controlled Release of Microquantities of Macromolecules", Cancer Drug Delivery, vol. 1, No. 2 pp. 119–123 (1984).

Ruoslahti et al., "New Perspectives in Cell Adhesion: RGD and Integrins", Science, vol. 238, pp. 491–497 (1987).

Van Der Lei et al., "Improved Healing of Small–Caliber Polytetrafluoroethylene Prostheses by Induction of a Clot Layer: A Review of Experimental Studies in Rats", Int. Angiol., vol. 10, No. 4, pp. 202–208 (1991).

"The Enlightened Response to a Changed Environment — The Duran Flexible Annuloplasty Ring", Medtronic Brochure (1989).

* cited by examiner

BIORESORBABLE ANNULOPLASTY PROSTHESIS

This is a continuation of application Ser. No. 08/551,352, filed Nov. 1, 1995, now abandoned.

FIELD OF THE INVENTION

This invention relates to biocompatible annuloplasty prostheses that are resorbed by the patient following implantation.

BACKGROUND OF THE INVENTION

Human heart valves comprise leaflets or cusps that open and close to control the flow of blood to a particular region of the heart. The mitral and tricuspid valves are located in the atrioventricular opening of the heart and function to prevent backflow of blood from the ventricle into the atrium when the ventricle contracts. The aortic valve is located between the left ventricle and the ascending aorta and functions to prevent backflow of blood into the left ventricle.

The mitral valve is located in the left atrioventricular opening of the heart. It includes two leaflets or cusps and is encircled by a dense fibrous ring known as the annulus. The anterior leaflet is located next to the aortic valve and is also known as the anterior medial leaflet. The posterior leaflet has a wider attachment to the annulus and is also known as the posterior lateral leaflet. The leaflets are held in place by chordae tendineae and papillary muscles. The commissure is the point at which the annular attachment of the leaflets meet and fuse. Coaptation refers to valve closure and the meeting of the free edges of the leaflets.

The tricuspid valve is located in the right atrioventricular opening and comprises three leaflets, sometimes referred to as the anterior, posterior and septal cusps (leaflets). These leaflets are roughly triangular in shape and, like the mitral valve leaflets, are attached to a fibrous ring, or annulus.

The aortic valve is composed of three segments, each of which is termed a semilunar cusp. The valve is closed during ventricular diastole and is open during systole.

The most common defect leading to mitral dysfunction is a dilation or elongation of the posterior two-thirds of the annulus, the section corresponding to the posterior leaflet. The anterior section of the annulus is anchored to the aortic root and is therefore not as subject to elongation. However, not infrequently in cases of mitral valve dysfunction, the anterior leaflet is displaced away from the center of the valve and is slightly thickened and shortened. Thus, in repairing a mitral valve, it is sometimes necessary to reduce the annulus to its physiological dimensions by repairing the dilated portion of the valve, to ensure coaptation. It may also be necessary to restore the commissure to its normal curvature and to reposition and reshape the anterior leaflet. Similar concepts apply to correction of tricuspid valve defects.

Mitral valve repair has been performed successfully since the late 1950's. Its appeal with cardiac surgeons, however, was not immediate. Only in more recent years, as surgeons have had appropriate devices to use and have increasingly realized the advantages of repair, has the proportion of mitral valves repaired increased. The clinical advantages of mitral valve repair as compared to replacement are attributed to better left ventricular function and the lack of need for long-term anticoagulation therapy. Better left ventricular function has led to a lower incidence of mitral valve stenosis and regurgitation for repair as compared to replacement procedures. The incidences of thromboembolism, hemorrhagic complications and infective endocarditis have been shown to be lower after mitral valve repair than after replacement. Actuarial survival after repair is also greater than that after valve replacement. Akins et al., *Ann. Thora. Surgery* 58: 668–76 (1994).

Annuloplasty, or annulus repair, has become an intermediate measure between non-invasive management of valvular heart disease and replacement of an entire heart valve with a prosthetic implant. Annuloplasty prostheses, for example ring-shaped devices, are used in the procedures and represent the standard method of repair. As clinical results increasingly show that annuloplasty prostheses better preserve left ventricular function, surgeons have become more enthusiastic about annuloplasty repair over valve replacement whenever feasible.

Annuloplasty prostheses differ from prosthetic heart valves in that the prostheses are designed to support diseased or damaged natural heart valves rather than replace them. An annuloplasty prosthesis is a device implanted around or in association with the mitral, tricuspid or aortic valve for reconstructive repair of valvular insufficiency. The indications for repair using annuloplasty prostheses include correction of annular dilatation, increases in leaflet coaptation, reinforcement of annular suture lines and prevention of future dilatation.

Annuloplasty prostheses are relatively new medical devices. The first annuloplasty prosthesis, designed by cardiovascular surgeon Dr. Alain Carpentier, was introduced in the early 1980's. Several other designs, including one by Professor Carlos Duran, followed shortly thereafter. Annuloplasty prostheses consist of three types: rigid, semi-flexible and flexible. Currently available rigid or flexible prostheses may be entirely composed of a biocompatible fabric (classified as flexible) such as polyester. Alternatively, a prosthesis may constitute a multiple component system composed of a more rigid core such as titanium, polyethylene or silicone, which is then covered by a fabric (classified as rigid or flexible depending on the core material). Some of the prostheses are made radiopaque through use of metal or by impregnating polymers with barium sulfate ($BaSO_4$).

The Carpentier-Edwards® ring (see, e.g. U.S. Pat. No. 5,061,277) is classified as rigid. This prosthesis is kidney shaped with one long curved segment corresponding to the posterior annulus; the ring is open in the portion corresponding to the anterior leaflet. It is constructed of a titanium alloy core with a sewing ring margin that consists of silicone rubber covered with polyester knit fabric. The Medtronic-Duran ring (Duran et al., *Circulation* (Suppl. I) 78:91–96 (1989)) is classified as flexible and, like the Carpentier ring, is not adjustable after implantation. It is constructed of a radiopaque core of silicone elastomer impregnated with ($BaSO_4$), and covered by polyester. It is claimed that this prosthesis can adapt to change in the mitral annulus, permitting optimal hemodynamics in diastole while maintaining coaptation and valve integrity in systole. The Puig-Massana Ring (see, e.g. U.S. Pat. No. 4,290,151) is a flexible and adjustable prosthesis that is also constructed of a core of silicone elastomer impregnated with ($BaSO_4$). The adjustability feature is not fully functional since the ring slips under the suture line resulting in equalization of tension around the entire ring. The Carpentier-Edwards Physio™ Annuloplasty Ring (see, e.g., U.S. Pat. No. 5,104,407) is a semi-rigid prosthesis that combines support for valve repair, yet has flexible properties allowing dynamic movement throughout the cardiac cycle. Other prostheses include partial rings (e.g., Cosgrove-EdwardS™, U.S. Pat. No. 5,290,300) which are constructed of polyester and are intended to be used only in the posterior mitral annular segment.

The ability of the valve to change shape during the cardiac cycle influences hemodynamic performance. It has been reported that the mitral annulus dilates 20% to 50% during diastole. Ormiston et al., *Circulation* 64:113–120 (1981). The hemodynamics seen with flexible prostheses 2 to 3 months following implantation have been reported to be better than that seen for rigid prostheses. However, by one year post-implantation the hemodynamics are the same for both groups. This may be due to tissue encapsulation of the prosthesis, thereby affecting its flexibility. However, the data do indicate that there may be less post-surgical morbidity and mortality with flexible prostheses than that seen with rigid prostheses. David, *Ann. Thorac. Surg.* 47:524–528 (1989). Rigid prostheses can prevent the ventricle from working efficiently by restricting annulus motion. In addition, rigid prostheses are more likely to dehisce than flexible devices. Dehiscence is due to the normal movement of the mitral valve annulus during systole and diastole and the resultant tension on the suture lines. Cohn, *Ann. Thorac. Surg.*, 45:284–290 (1988). Rigid prostheses also have a higher incidence of systolic anterior motion (SAM) of the mitral valve that can cause subaortic stenosis.

Suturing techniques for annuloplasty prostheses may vary depending on the design or the physician's preference. The suture may be placed around the prosthesis or passed through a portion of the prosthesis. Surgeons generally use either interrupted single or mattress sutures, or a continuous running suture similar to that used in prosthetic valve replacement.

An important drawback of all the currently available annuloplasty prostheses is that they are constructed of nonbiodegradable materials which, as discussed above, eventually are encapsulated by tissue and become rigid. This may lead to a stenotic valve that has suboptimal hemodynamics. Ideally, a bioresorbable annuloplasty prosthesis allows a natural, physiologically functional annulus to be reformed.

SUMMARY OF THE INVENTION

The invention relates to an annuloplasty prosthesis for use in remodeling a diseased annulus of a natural heart valve, comprising a biocompatible, resorbable member that is sized and shaped to extend about at least a substantial portion of the circumference of the annulus. Following surgical implantation, the member is resorbed at a rate allowing regeneration of reinforcing tissue in the annulus. The member can be adapted to function at the tricuspid, mitral or aortic valve positions of the heart. In one embodiment, the member may be sized and shaped to extend about less than the whole of the circumference of an annulus. Such an "open" or "non-continuous" member has opposed, spaced apart ends, the annular arcuate spacing between the ends being not less than about 1% and not more than about 50% of the whole of the circumference.

The member may comprise a biocompatible, resorbable polymer. The polymer can be composed of, without limitation, dextran, hydroxyethyl starch, gelatin, derivatives of gelatin, polyvinylpyrolidone, polyvinyl alcohol, poly[N-(2-hydroxypropyl)methacrylamide], polyglycols, polyesters, poly (orthoesters), poly (esteramides) and polyanhydrides. The polyesters can include, without limitation, poly (hydroxy acids) and copolymers thereof, poly ([epsilon]-caprolactone), poly (dimethyl glycolic acid) and poly (hydroxy butyrate). In a preferred embodiment, the polymer is selected from the group consisting of D,L-polylactic acid, L-polylactic acid, glycolic acid and copolymers of D,L-polylactic acid, L-polylactic acid, and glycolic acid.

The member may be manufactured to be of non-uniform rigidity. Preferably, the polymer of the member is invested with one or more biological response modifiers, including without limitation cell adhesion molecules, growth factors and differentiation factors.

The invention also includes a method for treating a patient having a diseased or defective tricuspid valve, comprising providing a resorbable annuloplasty prosthesis adapted for functioning at any one of the tricuspid, mitral or aortic valve positions of the heart, and surgically implanting the prosthesis in the heart of a patient.

DESCRIPTION OF THE PREFERRED EMBODIMENTS

Figure 1:
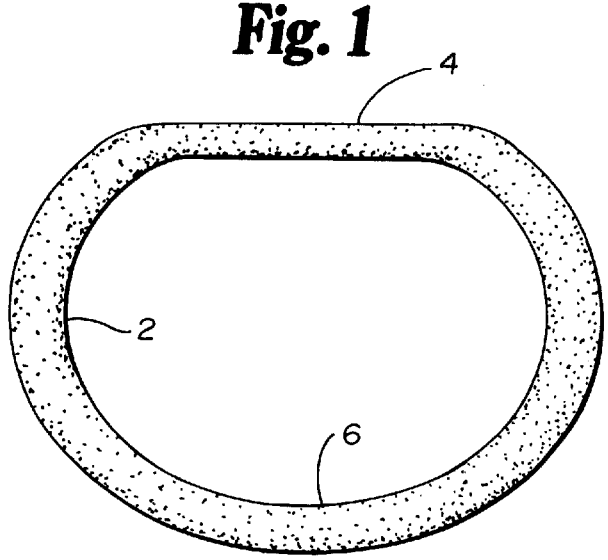
FIG. 1 depicts a "closed" or "continuous" embodiment of the bioresorbable annuloplasty prosthesis of the present invention.

The invention relates to annuloplasty prostheses used to correct tricuspid, mitral and aortic valve insufficiencies. The resorbable annuloplasty prosthesis of the present invention will allow reinforcement of the annular tissue for the time period necessary to achieve optimal regeneration of a natural annular structure. The regenerated tissue will completely replace the resorbable prosthesis, thereby leaving the recipient with a completely biological and functional annular structure that supports leaflet coaptation and optimal hemodynamics.

A bioresorbable annuloplasty prosthesis generally may be circular in cross section. The annuloplasty prosthesis may be continuous, or may be non-continuous. The shape of the prosthesis generally mimics the shape of the native annulus. The prosthesis can be designed to mimic the structural and functional properties of a healthy annulus. Specifically, the resorbable annuloplasty prosthesis has the following properties:

1. The bioresorbable prosthesis possesses sufficient mechanical properties to maintain coaptation and valve competence, but sufficient flexibility to permit good hemodynamics during diastole. The structural or functional properties may vary along the prosthesis to mimic the natural annular structure.
2. Prostheses may be manufactured in various sizes and shapes to accommodate the wide variation in annular morphologies.
3. The bioresorbable prosthesis degrades at a rate that allows substantially complete regeneration of the host annular structure. The resulting time period to resorption may be on the order of 4 to 6 months.
4. Tissue integration may be encouraged with the incorporation of biological response modifiers into the prosthesis. These substances include but are not limited to cell adhesion molecules, growth factors, differentiation factors and cytokines. In addition, heparin or other anticoagulants can be added to the prosthesis if blood compatibility is an issue. X-ray detectable substances can be incorporated into the prosthesis if desired.

5. An open cell structure (see below) allows rapid clot stabilization within the prosthesis, facilitating tissue ingrowth. A stable clot facilitates adhesion of the prosthesis to the host tissue and prevents peri-valvular leakage.

The main advantage of the bioresorbable annuloplasty prosthesis is that it encourages reinforcement of a diseased annulus with natural tissue rather than with foreign materials. The "naturally" remodeled tissue annulus has advantageous hemodynamic properties during diastole and allows sufficient leaflet coaptation during systole. Endocarditis that could occur during the remodeling phase may be minimized with the use of poly($\alpha$-hydroxy) acid bioresorbable polymers due to their ability to induce inflammatory leukocytes' bactericidal function. Devereux, D. F. et al., *J. of Surgery*, 162:243–246, 1991. Even in the situation in which the surgical implantation must be redone, there is no pre-existing implant to remove. The resorbable annuloplasty prosthesis is as easy to use and implant as other non-resorbable annuloplasty prostheses. Usually, the prosthesis is not manufactured to have an adjustable circumference, although such adjustability is not excluded from the prosthesis of the present invention.

The concept of a bioresorbable annuloplasty prosthesis that is substantially or completely replaced by functional annular tissue is new. All other annuloplasty prostheses are composed of non-resorbable materials that cause varying degrees of foreign body response long term, and which eventually become encapsulated by fibrous tissue. Such encapsulation can adversely affect function.

The resorbable annuloplasty prosthesis has mechanical properties sufficient to support the valve during implantation and during the post-implant healing period, while allowing the function of the adjacent structures, for example, the aorta, to be retained. Preferably the prosthesis is of sufficient flexibility such that the native compliance of the adjacent host structures (e.g., chordae tendineae, papillary muscles, aorta) and of the valve commissures is not significantly reduced.

Preferably, the bioresorbable material of the prosthesis resorbs, post implantation, at a rate that allows good tissue incorporation, but that also results in sufficient resorption within the normal post-operative period, approximately 4 to 6 months. A variety of resorbable, biocompatible materials, for example polymers, may be employed for manufacture of the prosthesis of the present invention. Homopolymers and copolymers such as those disclosed in U.S. Pat. No. 5,412,068, incorporated herein by reference, are appropriate for the resorbable prostheses of the present invention. Other polymers include without limitation dextran, hydroxyethyl starch, gelatin, derivatives of gelatin, polyvinylpyrolidone, polyvinyl alcohol, poly[N-(2-hydroxypropyl) methacrylamide], polyglycols, polyesters, poly (orthoesters), poly (esteramides) and polyanhydrides. Preferably the resorbable annuloplasty prostheses of the present invention are fashioned from polyesters such as poly (hydroxy acids) and copolymers thereof, poly ($\epsilon$-caprolactone), poly (dimethyl glycolic acid), or poly (hydroxy butyrate).

Most preferably the prostheses are manufactured of polymers of D,L-polylactic acid, L-polylactic acid, or glycolic acid, or copolymers of D,L-polylactic acid, L-polylactic acid, and glycolic acid. Such polymers may be manufactured as disclosed, for example, in U.S. Pat. No. 5,133,755, incorporated by reference herein.

It will be apparent to the ordinary skilled artisan that particular bioresorbable materials may be chosen to fit particular patient needs. For example, polymers may be chosen to be resorbed within the normal 4–6-month interval referenced above, but other polymers may be chosen to be resorbed within shorter or longer intervals. Variations in selected times to resorption may depend on, for example, the over-all health of the patient, variations in anticipated immune reactions of the patient to the implant, the site of implantation, and other clinical indicia apparent to the skilled artisan.

Preferably the fabricated resorbable prosthesis has an open, interconnected porosity allowing rapid clot stabilization and subsequent tissue ingrowth. The porous resorbable prosthesis may be fabricated using any of a variety of processes known to those of ordinary skill in the art, including a "replamineform" process, a positive replication process or common textile processes.

The replamineform process involves infiltrating a porous, inorganic structure (typically, calcium carbonate) with wax, dissolving the calcium carbonate, adding the appropriate monomer or mixture of monomers, polymerizing the monomers, and finally increasing the temperature to withdraw the wax. See, for example, Hiratzka et al., *Arch. Surgery* 114: 698–702 (1979), incorporated herein by reference. This process yields a positive copy of the porous, inorganic structure. Negative copies or casts of the porous inorganic structure may be made by filling the pores with a selected polymer, then dissolving the inorganic matrix (e.g., calcium carbonate) as a final step. What remains following completion of either the positive- or negative-cast steps of the replamineform process is a polymer with defined porosity.

A positive replication process is disclosed in, for example, Jamshidi et al., Resorbable Structured Porous Materials in the Healing Process of Hard Tissue Defects, *ASAIO* 34: 755–60 (1988), incorporated herein by reference. In principle, a positive replication process is very similar to the replamineform process.

In a further alternative embodiment, porosity can also be introduced into the prosthesis by mixing the polymer with particles of a specific size range (e.g., 20 to 300 micron diameters), then dissolving those particles during a final stage of the fabrication process. For example, sodium chloride crystals may be incorporated into a polymer or copolymer by adding crystals of the salt to a solution of dissolved polymer. After evaporating the solvent, annealing the polymer or copolymer by heating, and cooling at controlled rates, the sodium chloride crystals may be leached out. This leaves a porous polymer matrix. Porosity and pore size may be controlled by varying the concentration and size of the crystals. See, for example, Hubbell and Langer, *Chem. & Engineering News*, Mar. 13, 1995, pages 47–50, incorporated herein by reference.

The open porosity of the above-described resorbable prostheses provides a scaffold for cellular ingrowth. To facilitate ingrowth of host or other cells after implantation, a variety of biological response modifiers may be incorporated into the structure of the resorbable prosthesis. Biological response modifier molecules may be covalently or non-covalently coupled to the various internal and external surfaces defining the porosity of the resorbable prosthesis, or may be incorporated directly into the resorbable material during, for example, the polymerization process. In the latter case, the biological response modifier is slowly released as the prosthesis is resorbed.

Appropriate biological response modifiers may include, for example, cell adhesion molecules, cytokines including growth factors, and differentiation factors. Cell adhesion molecules (CAM) may be incorporated into the resorbable prosthesis in order to stimulate cell attachment, which is critical for normal cell function. Various CAM useful for incorporation include without limitation fibronectin, vitronectin, fibrinogen, collagen and laminin. See, e.g., Beck et al., *J. FASEB* 4: 148–160 (1990); Ruoslahti et al., *Science* 238: 491–97 (1987). The cell attachment activity has been isolated to specific amino acids sequences (expressed herein with standard singleletter code), for example RGD in the case of fibronectin, fibrinogen, collagen, osteopontin and others, REDV from fibronectin and YIGSR from laminin. Hubbell et al., *Bio/Technology* 9: 586–72 (1991); Humphries et al., *J. Cell Biol.* 103: 2637–47 (1986); Graf et al., *Cell* 48: 989–96 (1987). Other examples of cell attachment domains include the heparin-binding domains of fibronectin, KQAGDV and GPRP-containing peptides of fibrinogen and EILDV-containing peptides of fibronectin. Hynes et al., *Cell* 69: 11–25 (1992); Loike et al., *Proc. Natl. Acad. Sci. USA* 88: 1044–48 (1991). Thus, any cell attachment peptide-containing molecules functional as CAM for the cells seeded onto or migrating into the resorbable prosthesis may be incorporated into the prosthesis structure during or after fabrication.

Cellular ingrowth may be further facilitated through use of growth factors, including without limitation the fibroblast growth factors including acidic (FGF 1), basic (FGF 2) and FGF 3 through 9, platelet-derived growth factors including PDGF, PDGF-AA, PDGF-BB and PDGF-AB, transforming growth factors ($\beta1$–$\beta5$), epidermal growth factors including heparin-binding EGF, transforming growth factor $\alpha$ and other members of the epidermal growth factor family, the insulinlike growth factors I and II, platelet-derived endothelial cell growth factor and vascular endothelial growth factor. These factors have been shown to stimulate cellular migration (useful for attracting the appropriate cell population(s) into the prosthesis), proliferation (cell replication) and protein synthesis (required for production of extracellular matrix as the newly indwelling cells remodel the resorbing structure of the prosthesis). Albumin may be added to a particular growth factor to increase its effectiveness. Murray et al., *Cancer Drug Delivery* 1: 119 (1984).

Other biological response modifiers that may be incorporated into the resorbable annuloplasty prosthesis of the present invention include without limitation polysaccharides, mucopolysaccharides, glycoproteins, and glycosaminoglycans such as hyaluronic acid, chondroitin, chondroitin 4-sulfate, dermatan sulfate, keratan sulfate, heparin, heparan sulfate, alginate, poly-D-lysine, laminin and collagen types I, III and IV. It will be apparent to the ordinary skilled artisan that variations in individual biological response modifiers or combinations of biological response modifiers may be employed to suit the requirements of particular cell types, prosthesis materials, prosthesis configurations, sites of implantation and patient needs.

As described above, the bioresorbable prosthesis may be fabricated to have a structure conducive to formation of a stabilized blood clot after implantation. Such prostheses may have relatively high porosity, i.e., relatively high internal surface area (see above). Alternatively, the stabilized clot may be induced to form by inclusion of chemicals, e.g., coagulants, into the prosthesis structure as described above. Inducing a stabilized clot layer to form on the surface upon implantation facilitates cell ingrowth and healing, with the clot layer potentially functioning as a provisional matrix for healing, comparable to that occurring during normal vessel repair. Van Der Lei et al., *Int. Angiol.* 10: 202–08 (1991), for example, reported on the poor healing of expanded polytetrafluoroethylene prostheses in general, but also reported success in encouraging complete healing by inducing a clot layer to form on the graft surface upon implantation.

Referring now to the Figures, a resorbable annuloplasty prosthesis may be fashioned to have a generally oval shape similar to that of the native tissue annulus. For example, the prosthesis depicted in FIG. 1 is designed to conform to the shape of the base of the mitral valve, and has substantially the shape of a closed, continuous ring 2. Closed ring 2 may be circular, oval or, as shown, slightly straightened at 4 over a length of its periphery. Substantially straight portion 4 corresponds to the curvature of the anterior leaflet, and the opposite, complementary zone 6 corresponds to the curvature of the posterior leaflet. The prosthesis has in its plane an axis of symmetry, with its largest dimensions, along this axis and along a perpendicular axis, being generally between about 15 and 30 mm and about 15 and 40 mm respectively. Any given portion of the prosthesis may be generally circular in cross section, or may be oval or flattened in cross section.

Figure 2:
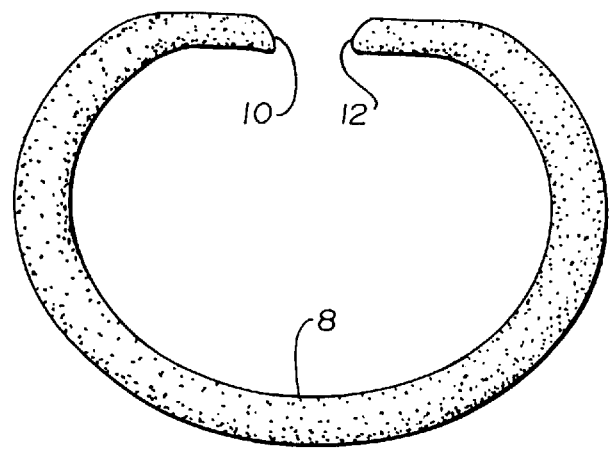
FIG. 2 depicts an "open" or "non-continuous" embodiment of the bioresorbable annuloplasty prosthesis of the present invention.

In an alternative embodiment as depicted in FIG. 2, the prosthesis may be in the form of an open, non-continuous ring 8 that is slightly straightened over a length of the periphery. A non-continuous design may be desired for hemodynamic performance and implant considerations. This part-annular-shaped prosthesis is open over a length generally between about 1% and 50 of the total annular shape. The free ends 10 and 12 of the open ring 8 are rounded or otherwise shaped so as not to damage the tissue in which they are disposed after implantation.

Figure 3:
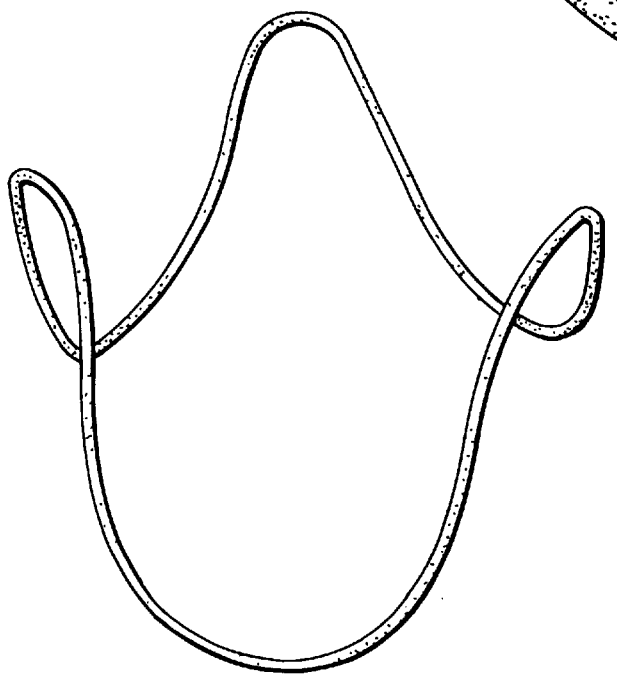
FIG. 3 depicts a ring-like annuloplasty prosthesis contoured and adapted for use in aortic valve repair.
Figure 4:
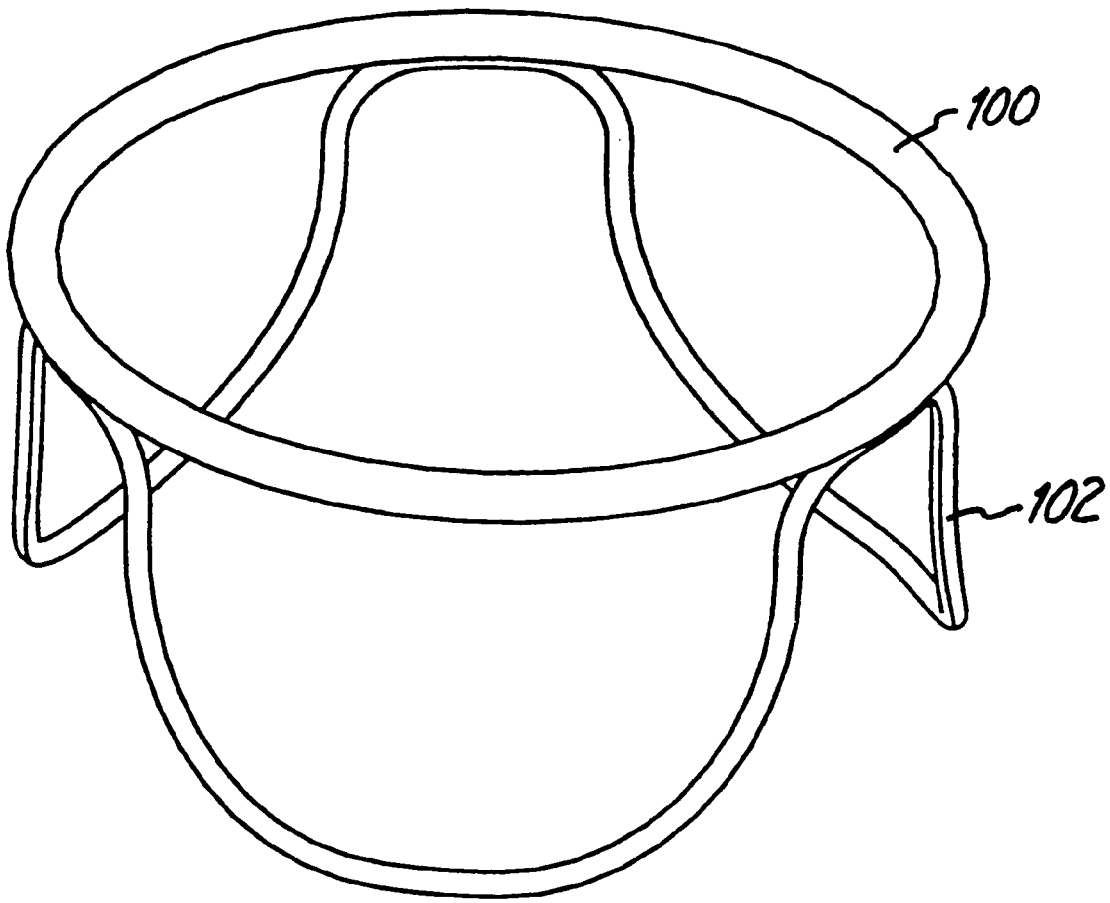
FIG. 4 depicts a ring-like annuloplasty prosthesis contoured and adapted for use in aortic valve repair including a collar.

It will be appreciated by the ordinary skilled artisan that the prosthesis of the present invention can be sized and shaped to any useful configuration appropriate to the mitral, tricuspid or aortic valve of an individual patient. For example, the prosthesis may be shaped generally as depicted in FIG. 3 so as to follow the contours of the commissures of the aortic valve, i.e., to be adapted to the trifoliate form of the aortic valvular orifice. In an alternative embodiment, an aortic valve annuloplasty prosthesis can be manufactured to include a sleeve or collar extending upward (with respect to the orientation depicted in FIG. 3), from along all or a substantial portion of the contour length. Referring to FIG. 4, in this orientation, the sleeve or collar 100 extends upward from the contoured ring-like prosthesis 102 into the aortic root or complex. The sleeve or collar 100 thereby facilitates attachment to and additional remodeling of the aortic complex above the commissures.

The resorbable material of the annuloplasty prosthesis preferably is flexible, with the flexibility selected and manufactured to approximate that of the native annulus and its supporting structure. As desired, the rigidity of the prosthesis (reflective of flexibility) may vary from one point to another on the prosthesis, i.e., the prosthesis may be of non-uniform rigidity. For example, more flexibility may be desired in the posterior part of the mitral valve annulus than the anterior part. This can be accomplished by controlling porosity of the matrix. In this manner, rigidity of the resorbable polymeric prosthesis material may be made to vary continuously from one region of the prosthesis to another region, or may vary in multiple step-wise increments from one region to another.

Any sutures used for attachment of the resorbable annuloplasty prosthesis to a patient may be bioresorbable. Preferably the resorption rate of the sutures is similar to that of the prosthesis.

A resorbable annuloplasty prosthesis of the present invention is implantable with a variety of surgical techniques appropriate to the configuration of the valvular tissue (e.g., annulus) and prosthesis and to the site of implantation. These surgical procedures will be apparent to the ordinary skilled artisan, and may include without limitation techniques such as disclosed in U.S. Pat. Nos. 3,656,185 and 4,042,979, incorporated herein by reference. Annuloplasty surgical procedures such as may be used with the annuloplasty prostheses of the present invention are also disclosed in Murphy et al., *Ann. Thorac. Surg.* 43: 52–8 (1987) and in Gorton et al., *Ann. Thorac. Surg.* 55: 860–3 (1993). Generally, a series of interrupted or continuous sutures is placed around the tissue annulus. The annuloplasty prosthesis is then parachuted down the sutures and tied in place. Following this, the cardiovascular incision (e.g., aortotomy) is then closed and the heart restarted.

With the resorbable annuloplasty prosthesis of the present invention, cross-clamp times for implantation will approximate those required with present annuloplasty rings, in which the prosthesis consists of non-resorbable materials.

The foregoing detailed description has been provided for a better understanding of the invention only and no unnecessary limitation should be understood therefrom as some modifications will be apparent to those skilled in the art without deviating from the spirit and scope of the appended claims.

What is claimed is:

1. An annuloplasty prosthesis for use in remodeling a diseased annulus of a natural heart valve, consisting essentially of a biocompatible, resorbable member that is sized and shaped to extend about at least a substantial portion of the circumference of said annulus, wherein, following surgical implantation, said member is resorbed at a rate allowing regeneration of reinforcing tissue in said annulus; wherein said prosthesis is adapted to function at the aortic valve position of the heart; wherein said member is shaped to follow the contours of the aortic valves commissures; wherein said member further includes a collar adapted for attachment to the aortic complex above said commissures, where said collar extends from said sized and shaped member.

2. An annuloplasty prosthesis for use in remodeling a diseased annulus of a natural heart valve, consisting essentially of a biocompatible, resorbable member that is sized and shaped to extend about at least a substantial portion of the circumference of said annulus, wherein, following surgical implantation, said member is resorbed at a rate allowing regeneration of reinforcing tissue in said annulus; wherein said member comprises a biocompatible, resorbable polymer; wherein said member is porous.

* * * * *